(12) United States Patent
Schiene et al.

(10) Patent No.: US 7,786,160 B2
(45) Date of Patent: Aug. 31, 2010

(54) COMBINATION OF SELECTED ANALGESICS AND COX-II INHIBITORS

(75) Inventors: Klaus Schiene, Duesseldorf (DE); Guenter Haase, Roetgen (DE); Babette-Yvonne Koegel, Langerwehe-Hamrich (DE); Elmar Friderichs, Stolberg (DE); Ulrich Jahnel, Langerwehe (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/133,190

(22) Filed: May 20, 2005

(65) Prior Publication Data

US 2005/0277687 A1    Dec. 15, 2005

Related U.S. Application Data

(63) Continuation of application No. PCT/EP03/12882, filed on Nov. 18, 2003.

(30) Foreign Application Priority Data

Nov. 22, 2002   (DE) ................. 102 54 785
Jun. 6, 2003    (DE) ................. 103 26 103

(51) Int. Cl.
 *A61K 31/415*    (2006.01)
 *A61K 31/135*    (2006.01)
(52) U.S. Cl. .............. 514/406; 514/650; 514/646; 514/506; 514/445
(58) Field of Classification Search ............ 514/646, 514/506, 620, 349, 369, 445, 406, 650
See application file for complete search history.

(56) References Cited

U.S. PATENT DOCUMENTS

| 5,330,761 A | 7/1994 | Baichwal |
|---|---|---|
| 5,399,362 A | 3/1995 | Baichwal et al. |
| 5,455,046 A | 10/1995 | Baichwal |
| 5,472,711 A | 12/1995 | Baichwal |
| 5,516,803 A | 5/1996 | Raffa |
| 5,733,936 A * | 3/1998 | Buschmann et al. ........ 514/646 |
| 6,344,558 B1 * | 2/2002 | Buschmann et al. .......... 544/86 |
| 2002/0132825 A1 | 9/2002 | Burch et al. |

FOREIGN PATENT DOCUMENTS

| DE | 33 09 516 A1 | 12/1983 |
|---|---|---|
| DE | 44 26 245 A | 2/1996 |
| DE | 195 25 137 A | 1/1997 |
| EP | 1 219 594 | 7/2002 |
| WO | WO 00 51685 | 9/2000 |
| WO | WO 01 49654 | 7/2001 |
| WO | WO 02 28817 | 4/2002 |

OTHER PUBLICATIONS

Souillac et al. Characterization of delivery systems, differential scanning calorimetry, pp. 217-218 (in Encyclopedia of Controoled Drug Delivery, 1999, John Wiley & Sons, pp. 212-227).*
Vippagunta et al. Advanced Drug Delivery Reviews, 48 (2001), pp. 3-26.*
T. Issiouri et al., "The Efficacy of Premedication with Celecoxib and Acetaminophen in Preventing Pain After Otolaryngologic Surgery", Anesth. Analg., May 2002, p. 1188, vol. 94.
Raymond Sinatra, MD, PhD, "Role of COX-2 Inhibitors in the Evolution of Acute Pain Management", Journal of Pain and Symptom Management, Jul. 15, 2002, pp. S18-S27, vol. 24, No. 15, US Cancer Pain Relief Committee, Elsevier, New York, New York, USA.
German Office Action dated Oct. 23, 2003.

* cited by examiner

*Primary Examiner*—Jennifer M Kim
(74) *Attorney, Agent, or Firm*—Crowell & Moring LLP (57) ABSTRACT

Combinations of certain analgesics with certain COX-II inhibitors, related pharmaceutical compositions, including advantageous galenical forms containing these combinations, and to the use thereof in methods of treatment, in particular for the treatment of pain.

11 Claims, 5 Drawing Sheets

COMBINATION OF SELECTED ANALGESICS AND COX-II INHIBITORS

CROSS REFERENCE TO RELATED APPLICATIONS

This application is a continuation of International Patent Application No. PCT/EP2003/012882, filed Nov. 18, 2003, designating the United States of America, and published in German as WO 2004/047823 A1, the entire disclosure of which is incorporated herein by reference. Priority is claimed based on German Patent Application Nos. 102 54 785.8, filed Nov. 22, 2002, and 103 26 103.6, filed Jun. 6, 2003.

FIELD OF THE INVENTION

The invention relates to the combination of analgesics of group A with COX-II inhibitors of group B, pharmaceutical compositions, including advantageous galenical forms containing this combination, and to the use thereof, in particular for the treatment of pain.

BACKGROUND OF THE INVENTION

The treatment of chronic and non-chronic pain conditions is extremely important in medicine. There is currently a worldwide demand for additional, not exclusively opioid-based, but highly effective, pain treatment. The urgent need for action for patient-oriented and purposeful treatment of chronic and non-chronic pain conditions, this being taken to mean the successful and satisfactory treatment of pain for the patient, is documented in the large number of scientific papers which have recently appeared in the field of applied analgesics and fundamental research work on nociception.

Even if the analgesics that are conventionally used for treating pain, for example opioids, NA- and 5HT-reuptake inhibitors, NSAIDS and also COX inhibitors, are analgesically effective, side effects nevertheless sometimes occur, in particular in the case of the more active opioids.

SUMMARY OF THE INVENTION

One object of the present invention is therefore to provide substances or substance combinations that are suitable for the treatment of pain, that preferably simultaneously exhibit fewer side effects in the active doses than is known from the prior art and, in particular, in the combinations which exhibit a synergistic effect for the treatment of pain.

Surprisingly, it has been found that a combination of selected analgesics of group A with COX-II inhibitors exhibit an outstanding analgesic effect. Moreover, these combinations have exceeded expectations and, even in small doses, have proven so effective that it was possible to reduce the dose of the combined active ingredients. It is thus expected that there will be significantly fewer side effects than occur when larger doses are required.

Accordingly, the invention relates to an active ingredient combination comprising at least one analgesic compound A and at least one COX-II inhibitor, with compound A selected from:

group a) containing:
1-phenyl-3-dimethylamino-propane compounds according to general formula I wherein
X is selected from OH, F, Cl, H or OC(O)R$^7$, where R$^7$ is selected from branched or unbranched, saturated or unsaturated, unsubstituted or singly or multiply substituted C$_{1-3}$ alkyl, R$^1$ is selected from branched or unbranched, saturated or unsaturated, unsubstituted or singly or multiply substituted C$_{1-4}$ alkyl, R$^2$ and R$^3$ respectively independently of one another are selected from branched or unbranched, saturated or unsaturated, unsubstituted or singly or multiply substituted H or C$_{1-4}$ alkyl, or R$^2$ and R$^3$ together form a saturated, unsubstituted or singly or multiply substituted C$_{4-7}$cycloalkyl radical, R$^9$ to R$^{13}$ respectively independently of one another are selected from H, F, Cl, Br, I, CH$_2$F, CHF$_2$, CF$_3$, OH, SH, OR$^{14}$, OCF$_3$, SR$^{14}$, NR$^{17}$R$^{18}$, SOCH$_3$, SOCF$_3$; SO$_2$CH$_3$, SO$_2$CF$_3$, CN, COOR$^{14}$, NO$_2$, CONR$^{17}$R$^{18}$; branched or unbranched, saturated or unsaturated, unsubstituted or singly or multiply substituted C$_{1-6}$ alkyl; unsubstituted or singly or multiply substituted phenyl;

where R$^{14}$ is selected from C$_{1-6}$ alkyl; respectively unsubstituted or singly or multiply substituted pyridyl, thienyl, thiazolyl, phenyl, benzyl or phenethyl; PO(O—C$_{1-4}$ alkyl)$_2$, CO(OC$_{1-5}$ alkyl), CONH—C$_6$14-(C$_{1-3}$ alkyl), CO(C$_{1-5}$ alkyl), CO—CHR$^{17}$—NHR$^{18}$, CO—C$_6$H$_4$—R$^{15}$, where R$^{15}$ is ortho-OCOC$_{1-3}$ alkyl or meta- or para-CH$_2$N(R$^{16}$)$_2$ where R$^{16}$ is C$_{1-4}$ alkyl or 4-morpholino, wherein the alkyl groups in the radicals R$^{14}$, R$^{15}$ und R$^{16}$ may be branched or unbranched, saturated or unsaturated, unsubstituted or singly or multiply substituted;

R$^{17}$ and R$^{18}$ respectively independently of one another are selected from H; branched or unbranched, saturated or unsaturated, unsubstituted or singly or multiply substituted C$_{1-6}$ alkyl; respectively unsubstituted or singly or multiply substituted phenyl, benzyl or phenethyl, or

R$^9$ and R$^{10}$ or R$^{10}$ und R$^{11}$ together form an OCH$_2$O, OCH$_2$CH$_2$O, OCH=CH, CH=CHO, CH=C(CH3)O, OC(CH3)=CH, (CH$_2$)$_4$ or OCH=CHO ring, optionally in the form of their racemates, their pure stereoisomers, in particular enantiomers or diastereomers, or in the form of mixtures of the stereoisomers, in particular the enantiomers or diastereomers, in any mixing ratio; in the illustrated form or in the form of their acids or their bases or in the form of their salts, in particular the physiologically acceptable salts, or in the form of their solvates, in particular the hydrates;

group b) containing:

substituted 6-dimethyl aminomethyl-1-phenyl-cyclohexane compounds according to general formula II

II wherein

X is selected from OH, F, Cl, H or OC(O)$R^7$, where $R^7$ is selected from branched or unbranched, saturated or unsaturated, unsubstituted or singly or multiply substituted $C_{1-3}$ alkyl, $R^1$ is selected from $C_{1-4}$ alkyl, benzyl, $CF_3$, OH, $OCH_2$—$C_6H_5$, O—$C_{1-4}$ alkyl, Cl or F and $R^9$ to $R^{13}$ respectively independently of one another are selected from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; branched or unbranched, saturated or unsaturated, unsubstituted or singly or multiply substituted $C_{1-6}$ alkyl; unsubstituted or singly or multiply substituted phenyl;

where $R^{14}$ is selected from $C_{1-6}$ alkyl; respectively unsubstituted or singly or multiply substituted pyridyl, thienyl, thiazolyl, phenyl, benzyl or phenethyl; PO(O—$C_{1-4}$ alkyl)$_2$, CO(O$C_{1-5}$ alkyl), CONH—$C_6H_4$-($C_{1-3}$ alkyl), CO($C_{1-5}$ alkyl), CO—$CHR^{17}$—$NHR^{18}$, CO—$C_6H_4$—$R^{15}$, where $R^{15}$ is ortho-OCO$C_{1-3}$ alkyl or meta- or para-$CH_2N(R^{16})_2$ where $R^{16}$ is $C_{1-4}$ alkyl or 4-morpholino, wherein the alkyl groups in the radicals $R^{14}$, $R^{15}$ and $R^{16}$ may be branched or unbranched, saturated or unsaturated, unsubstituted or singly or multiply substituted;

where $R^{17}$ and $R^{18}$ respectively independently of one another are selected from H; branched or unbranched, saturated or unsaturated, unsubstituted or singly or multiply substituted $C_{1-6}$ alkyl; respectively unsubstituted or singly or multiply substituted phenyl, benzyl or phenethyl, or

$R^9$ and $R^{10}$ or $R^{10}$ and $R^{11}$ together form an $OCH_2O$, $OCH_2CH_2O$, OCH=CH, CH=CHO, CH=C(CH3)O, OC(CH3)=CH, $(CH_2)_4$ or OCH=CHO ring, optionally in the form of their racemates, their pure stereoisomers, in particular enantiomers or diastereomers, or in the form of mixtures of the stereoisomers, in particular the enantiomers or diastereomers, in any mixing ratio; in the illustrated form or in the form of their acids or their bases or in the form of their salts, in particular the physiologically acceptable salts, or in the form of their solvates, in particular the hydrates;

and/or group c) containing:

6-dimethyl aminomethyl-1-phenyl-cyclohexane compounds according to general formula III

III wherein

X is selected from OH, F, Cl, H or OC(O)$R^7$, where $R^7$ is selected from branched or unbranched, saturated or unsaturated, unsubstituted or singly or multiply substituted $C_{1-3}$ alkyl, and $R^9$ to $R^{13}$ respectively independently of one another are selected from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; branched or unbranched, saturated or unsaturated, unsubstituted or singly or multiply substituted $C_{1-6}$ alkyl; unsubstituted or singly or multiply substituted phenyl; where $R^{14}$ is selected from $C_{1-6}$ alkyl; respectively unsubstituted or singly or multiply substituted pyridyl, thienyl, thiazolyl, phenyl, benzyl or phenethyl; PO(O—$C_1$-4 alkyl)$_2$, CO(O$C_{1-5}$ alkyl), CONH—$C_6H_4$-($C_{1-3}$ alkyl), CO($C_{1-5}$ alkyl), CO—$CHR^{17}$—$NHR^{18}$, CO—$C_6H_4$—$R^{15}$, where $R^{15}$ is ortho-OCO$C_{1-3}$ alkyl or meta- or para-$CH_2N(R^{16})_2$ where $R^{16}$ is $C_{1-4}$ alkyl or 4-morpholino, wherein the alkyl groups in the radicals $R^{14}$, $R^{15}$ and $R^{16}$ may be branched or unbranched, saturated or unsaturated, unsubstituted or singly or multiply substituted;

where $R^{17}$ and $R^{18}$ respectively independently of one another are selected from H; branched or unbranched, saturated or unsaturated, unsubstituted or singly or multiply substituted $C_{1-6}$ alkyl; respectively unsubstituted or singly or multiply substituted phenyl, benzyl or phenethyl, or $R^9$ and $R^{10}$ or $R^{10}$ and $R^{11}$ together form an $OCH_2O$, $OCH_2CH_2O$, OCH=CH, CH=CHO, CH=C(CH3)O, OC(CH3)=CH, $(CH_2)_4$ or OCH=CHO ring, with the condition with that if $R^9$, $R^{11}$ and $R^{13}$ correspond to H, and one of $R^{10}$ or $R^{12}$ corresponds to H and the other to $OCH_3$, X may not be OH, optionally in the form of their racemates, their pure stereoisomers, in particular enantiomers or diastereomers, or in the form of mixtures of the stereoisomers, in particular the enantiomers or diastereomers, in any mixing ratio; in the illustrated form or in the form of their acids or their bases or in the form of their salts, in particular the physiologically acceptable salts, or in the form of their solvates, in particular the hydrates.

In the context of this invention, alkyl and cycloalkyl radicals are taken to mean saturated and unsaturated (but not aromatic), branched, unbranched and cyclic hydrocarbons which may be unsubstituted or singly or multiply substituted. In this case $C_{1-2}$ alkyl represents C1 or C2 alkyl, $C_{1-3}$ alkyl represents C1, C2 or C3 alkyl, $C_{1-4}$ alkyl represents C1, C2, C3 or C4 alkyl, $C_{1-5}$ alkyl represents C1, C2, C3, C4 or C5 alkyl, C1-6 alkyl represents C1, C2, C3, C4, C5 or C6 alkyl, $C_{1-7}$ alkyl represents C1, C2, C3, C4, C5, C6 or C7 alkyl, $C_{1-8}$ alkyl represents C1, C2, C3, C4, C5, C6, C7 or C8 alkyl, $C_{1-10}$ alkyl represents C1, C2, C3, C4, C5, C6, C7, C8, C9 or C10 alkyl and $C_{1-18}$ alkyl represents C1, C2, C3, C4, C5, C6, C7, C8, C9, C10, C11, C12, C13, C14, C15, C16, C17 or C18 alkyl. Furthermore $C_{3-4}$ cycloalkyl represents C3 or C4 cycloalkyl, $C_{3-5}$ cycloalkyl represents C3, C4 or C5 cycloalkyl, $C_{3-6}$ cycloalkyl represents C3, C4, C5 or C6 cycloalkyl, $C_{3-7}$ cycloalkyl represents C3, C4, C5 or C7 cycloalkyl, $C_{3-8}$ cycloalkyl represents C3, C4, C5, C6, C7 or C8 cycloalkyl, $C_{4-5}$ cycloalkyl represents C4 or C5 cycloalkyl, $C_{4-6}$ cycloalkyl represents C4, C5 or C6 cycloalkyl, $C_{4-7}$ cycloalkyl represents C4, C5, C6 or C7 cycloalkyl, $C_{5-6}$ cycloalkyl represents C5 or C6 cycloalkyl and $C_{5-7}$ cycloalkyl represents C5, C6 or C7 cycloalkyl. With respect to cycloalkyl, the term also comprises saturated cycloalkyls, in which one or two carbon atoms are replaced by a heteroatom, S, N or O. However, the term cycloalkyl also includes singly or multiply, preferably singly, unsaturated cycloalkyls without a heteroatom in the ring, if the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ and pyrazolinone, oxopyrazolinone, [1,4]dioxan or dioxolan.

In this case, in conjunction with alkyl and cycloalkyl—unless this is not explicitly defined otherwise—the term substituted in the context of this invention denotes the substitution of at least one (optionally also more) hydrogen radical(s) for F, Cl, Br, I, $NH_2$, SH, $OCH_3$, $SCH_3$, $N(CH_3)_2$, $NHCH_3$ or OH, wherein "multiply substituted" or "substituted" with multiple substitution denotes that the substitution is made both on different and on the same atoms multiply with the same or different substituents, for example threefold on the same carbon atom as in the case of $CF_3$ or at different points as in the case of —CH(OH)—CH=CH—$CHCl_2$. Particularly preferred substituents in this case are F, Cl and OH. With respect to cycloalkyl, the hydrogen radical can also be replaced by $OC_{1-3}$ alkyl or $C_{1-3}$ alkyl (singly or multiply substituted or unsubstituted respectively), in particular methyl, ethyl, n-propyl, i-propyl, $CF_3$, methoxy or ethoxy.

The term $(CH_2)_{3-6}$ is taken to mean —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—, $(CH_2)_{1-4}$ to mean —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ to mean —$CH_2$—$CH_2$—$CH_2$—$CH_2$— and —$CH_2$—$CH_2$—$CH_2$—$CH_2$—$CH_2$—, etc.

An aryl radical denotes ring systems with at least one aromatic ring but without heteroatoms even in only one of the rings. Examples are phenyl, naphthyl, fluoroanthenyl, fluorenyl, tetralinyl or indanyl, which can be unsubstituted or singly or multiply substituted.

A heteroaryl radical denotes heterocyclic ring systems with at least one unsaturated ring, which contain one or more heteroatoms from the group comprising nitrogen, oxygen and/or sulphur and which can also be singly or multiply substituted. Examples from the group of heteroaryls include furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolan, benzodioxan, carbazole, indole and quinazoline.

In this case, in conjunction with aryl and heteroaryl, substituted denotes the substitution of the aryl or heteroaryl by $R^{22}$, $OR^{22}$, a halogen, preferably F and/or Cl, a $CF_3$, a CN, a $NO_2$, a $NR^{23}R^{24}$, a $C_{1-6}$ alkyl (saturated), a $C_{1-6}$ alkoxy, a $C_{3-8}$cycloalkoxy, a $C_{3-8}$ cycloalkyl or a $C_{2-6}$ alkylene.

In this case the radical $R^{22}$ represents H, a $C_{1-10}$ alkyl, preferably a $C_{1-6}$ alkyl, an aryl or heteroaryl radical or an aryl or heteroaryl radical bound by $C_{1-3}$ alkyl, saturated or unsaturated, or a $C_{1-3}$ alkylene-group-bound aryl or heteroaryl radical, wherein these aryl or heteroaryl radicals must not themselves be substituted by aryl or heteroaryl radicals, the radicals $R^{23}$ und $R^{24}$, which may be the same or different, represent H, a $C_{1-10}$ alkyl, preferably a $C_{1-6}$ alkyl, an aryl radical, a heteroaryl radical or an aryl or heteroaryl radical bound by saturated or unsaturated $C_{1-3}$ alkyl or a $C_{1-3}$ alkylene-group-bound aryl or heteroaryl radical, wherein these aryl or heteroaryl radicals must not themselves be substituted by aryl or heteroaryl radicals, or the radicals $R^{23}$ and $R^{24}$ together mean $CH_2CH_2OCH_2CH_2$, $CH_2CH_2NR^{25}CH_2CH_2$ or $(CH_2)_{3-6}$, and the radical $R^{25}$ represents H, a $C_{1-10}$ alkyl, preferably a $C_{1-6}$ alkyl, an aryl radical, a heteroaryl radical or an aryl or heteroaryl radical bound by saturated or unsaturated $C_{1-3}$ alkyl or a $C_{1-3}$ alkylene-group-bound aryl or heteroaryl radical, wherein these aryl or heteroaryl radicals must not themselves be substituted by aryl or heteroaryl radicals.

The term "salt" denotes any form of the active ingredient according to the invention in which it assumes or is charged with an ionic form and is coupled to a counter ion (a cation or anion) or is in solution. This also includes complexes of the active ingredient with other molecules and ions, in particular complexes which are complexed by ion interaction. In particular this is taken to mean (and this is also a preferred embodiment of this invention) physiologically acceptable salts, in particular physiologically acceptable salts with cations or bases and physiologically acceptable salts with anions or acids or even a salt formed with a physiologically acceptable acid or physiologically acceptable cation.

The "term physiologically acceptable salt with anions or acids" denotes, in the context of this invention, salts of at least one of the compounds according to the invention—usually protonated, for example on nitrogen—as a cation with at least one anion which are physiologically acceptable—in particular when administered to humans and/or mammals. In the context of this invention this denotes, in particular, the salt formed with a physiologically acceptable acid, namely salts of the respective active ingredient with inorganic or organic acids, which are physiologically acceptable—in particular when administered to humans and/or mammals. Examples of physiologically acceptable salts of specific acids are salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1b6-benzo[d]isothiazol-3-one (saccharic acid), monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, acetylsalicylic acid, hippuric acid and/or aspartic acid. Hydrochloride salt and citrate are particularly preferred.

The term "salt formed with a physiologically acceptable acid", according to this invention, is taken to mean salts of the respective active ingredient with inorganic or organic acids which are physiologically acceptable—in particular when administered to humans and/or mammals. Hydrochloride and citrate are particularly preferred. Examples of physiologically acceptable acids include: hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid, 1,1-dioxo-1,2-dihydro1b6-benzo[d]isothiazol-3-one (saccharic acid), monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, acetylsalicylic acid, hippuric acid and/or aspartic acid. Hydrochloride salt and citrate are particularly preferred.

The term "salt formed with a physiologically acceptable acid", in the context of this invention, is taken to mean salts of the respective active ingredient with inorganic or organic acids which are physiologically acceptable—in particular when administered to humans and/or mammals. Hydrochloride and citrate are particularly preferred. Examples of physiologically acceptable acids include: hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid, 1,1-dioxo-1,2-dihydro1$\lambda^6$-benzo[d]isothiazol-3-one (saccharic acid), monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, acetylsalicylic acid, hippuric acid and/or aspartic acid.

The term "physiologically acceptable salt with cations or bases" denotes, in the context of this invention, salts of at least one of the compounds according to the invention—usually a (deprotonated) acid—as an anion with at least one, preferably inorganic, cation, which are physiologically acceptable, in particular when administered to humans and/or mammals. The salts of the alkali and alkaline-earth metals are particularly preferred, but also $NH_4^+$, in particular however (mono) or (di) sodium, (mono) or (di) potassium, magnesium or calcium salts.

The term "salt formed with a physiologically acceptable cation" is taken to mean, in the context of this invention, salts of at least one of the respective compounds as an anion with at least one inorganic cation, which are physiologically acceptable, in particular when administered to humans and/or mammals. The salts of the alkali and alkaline-earth metals are particularly preferred, but also $NH_4^+$, in particular however (mono) or (di) sodium, (mono) or (di) potassium, magnesium or calcium salts.

Compounds of group a) and the production thereof are known from DE 44 26 245 A1. Compounds of group b) and c) and the production thereof are known from DE 195 25 137 A1.

The term "COX-II inhibitors" refers to selective inhibitors of COX II, the inducible isoform of cyclooxygenase. Cyclooxygenase is a synonym for prostaglandin endoperoxide synthase; an enzyme that combines the function of a dioxgenase and a peroxidase and, as a key enzyme, catalyses the conversion of arachidonic acid into prostaglandin H2 or peroxides (see Walter de Gruyter, Pschyrembel, 258th edition; Roche Lexikon Medizin, 4th edition). Further information regarding COX-II inhibitors, in particular listings thereof, may be found on pp. 13 to 126 and in particular 21 to 31 of "Analgesics, From Chemistry and Pharmacology to Clinical Application"; Buschmann et al (eds.), 1st edition, Wiley-VCH, 2002. All of the content of this chapter is part of the description of this invention. The term "COX-II inhibitors" refers in particular, by way of example, to Celecoxib, Rofecoxib, Etoricoxib, Valdecoxib, Parecoxib, Etodolac, Meloxicam or Nimesulide. Celecoxib, which is sold under the name LOSEC® or Prilosec® or CELEBREX®, and Rofecoxib, which is sold under the name VIOXX®, are of particular importance. The term "selectively correspondingly preferred" denotes that the compound displays more pronounced inhibition of COX II than of COX I and/or in particular exhibits an $IC_{50}$ that is ≧5 lower on COX II than on COX 1.

In a preferred embodiment, for the combination according to the invention, compound A in group a) is selected from compounds according to formula I, in which:

X is selected from

OH, F, Cl, $OC(O)CH_3$ or H, preferably OH, F, $OC(O)CH_3$ or H, and/or $R^1$ is selected from saturated and unsubstituted, branched or unbranched $C_{1-4}$ alkyl; preferably $CH_3$, $C_2H_5$, $C_4H_9$ or t-butyl, in particular $CH_3$ or $C_2H_5$, and/or $R^2$ and $R^3$ independently of one another are selected from saturated and unsubstituted, branched or unbranched H, $C_{1-4}$ alkyl; preferably H, $CH_3$, $C_2H_5$, i-propyl or t-butyl, in particular H or $CH_3$, preferably $R^3$=H, or $R^2$ and $R^3$ together form a saturated or unsaturated, unsubstituted or singly or multiply substituted, preferably saturated and unsubstituted $C_{5-6}$ cycloalkyl radical, in particular cyclohexyl.

and/or $R^9$ to $R^{13}$, wherein three or four of the radicals $R^9$ to $R^{13}$ must correspond to H, independently of one another are selected from H, Cl, F, OH, $CF_2H$, $CF_3$ or saturated and unsubstituted, branched or unbranched $C_{1-4}$ alkyl; $OR^{14}$ or $SR^{14}$, where $R^{14}$ is selected from saturated and unsubstituted, branched or unbranched $C_{1-3}$ alkyl;

preferably H, Cl, F, OH, $CF_2H$, $CF_3$, $OCH_3$ or $SCH_3$ or $R^{12}$ and $R^{11}$ form a 3,4—OCH=CH ring in particular if $R^9$, $R^{11}$ and $R^{13}$ correspond to H, one of $R^{10}$ or $R^{12}$ also corresponds to H, whereas the other is selected from:

Cl, F, OH, $CF_2H$, $CF_3$, $OR^{14}$ or $SR^{14}$, preferably OH, $CF_2H$, $OCH_3$ or $SCH_3$ or if $R^9$ and $R^{13}$ correspond to H and $R^{11}$ corresponds to OH, $OCH_3$, Cl or F, preferably Cl, one of $R^{10}$ or $R^{12}$ also corresponds to H, whereas the other corresponds to OH, $OCH_3$, Cl or F, preferably Cl, or if $R^9$, $R^{10}$, $R^{12}$ and $R^{13}$ correspond to H, $R^{11}$ is selected from $CF_3$, $CF_2H$, Cl or F, preferably F, or If $R^{10}$, $R^{11}$ and $R^{12}$ correspond to H, one of $R^9$ or $R_{13}$ also corresponds to H, whereas the other is selected from OH, $OC_2H_5$ or $OC_3H_7$.

In particular for compounds of group a), compounds of formula 1, wherein $R^3$=H, are in the form of the diastereomers having the relative configuration Ia Ia in particular in mixtures having a relatively high content of this diastereomer in comparison to the other diastereomer, or are used as a pure diastereomer.

In particular for compounds of group a), compound A, which is selected from the following group, is used:
- (2RS,3RS)-1-dimethylamino-3-(3-methoxy-phenyl)-2-methyl-pentan-3-ol,
- (+)-(2R,3R)-1-dimethylamino-3-(3-methoxy-phenyl)-2-methyl-pentan-3-ol,
- (2RS,3RS)-3-(3,4-dichlorophenyl)-1-dimethylamino-2-methyl-pentan-3-ol,
- (2RS,3RS)-3-(3-difluoromethyl-phenyl)-1-dimethylamino-2-methyl-pentan-3-ol,
- (2RS,3RS)-1-dimethylamino-2-methyl-3-(3-methylsulphanylphenyl)-pentan-3-ol,
- (3RS)-1-dimethylamino-3-(3-methoxy-phenyl)4,4-dimethyl-pentan-3-ol,
- (2RS,3RS)-3-(3-dimethylamino-1-ethyl-1-hydroxy-2-methyl-propyl)-phenol,
- (1RS,2RS)-3-(3-dimethylamino-1-hydroxy-1,2-dimethyl-propyl)-phenol,
- (+)-(1R,2R)-3-(3-dimethylamino-1-hydroxy-1,2-dimethyl-propyl)-phenol,
- (+)-(1R,2R)-3-(3-dimethylamino-1-hydroxy-1,2-dimethyl-propyl)-phenol,
- (−)-(1R,2R)-3-(3-dimethylamino-1-ethyl-2-methyl-propyl)-phenol,
- (+)-(1R,2R)-acetic acid-3-dimethylamino-1-ethyl-1-(3-methoxy-phenyl)-2-methyl-propylester,
- (1RS)-1-(1-dimethylaminomethyl-cyclohexyl)-1-(3-methoxy-phenyl)-propan-1-ol,
- (2RS,3RS)-3-(4-chlorophenyl)-1-dimethylamino-2-methyl-pentan-3-ol,
- (+)-(2R,3R)-3-(3-dimethylamino-1-ethyl-1-hydroxy-2-methyl-propyl)-phenol,
- (2RS,3RS)4-dimethylamino-2-(3-methoxy-phenyl)-3-methyl-butan-2-ol
- (+)-(2R,3R)4-dimethylamino-2-(3-methoxy-phenyl)-3-methyl-butan-2-ol, preferably as the hydrochloride.

In a preferred embodiment, for the combination according to the invention, compound A in group b) is selected from compounds according to formula II, in which:

X is selected from
OH, F, Cl, OC(O)CH$_3$ or H, preferably OH, F or H, in particular OH, and/or R$^1$ is selected from
C$_{1-4}$ alkyl, CF$_3$, OH, O—C$_{1-4}$ alkyl, Cl or F, preferably OH, CF$_3$ or CH$_3$, and/or R$^9$ to R$^{13}$, wherein three or four of the radicals R$^9$ to R$^{13}$ must correspond to H, independently of one another are selected from H, Cl, F, OH, CF$_2$H, CF$_3$ or saturated and unsubstituted, branched or unbranched C$_{1-4}$ alkyl; OR$^{14}$ or SR$^{14}$, where R$^{14}$ is selected from saturated and unsubstituted, branched or unbranched C$_{1-3}$ alkyl;

preferably H, Cl, F, OH, CF$_2$H, CF$_3$, OCH$_3$ or SCH$_3$ or R$^{12}$ and R$^{11}$ form a 3,4-OCH=CH ring, in particular if R$^9$, R$^{10}$ and R$^{13}$ correspond to H, one of R$^{10}$ or R$^{12}$ also corresponds to H, whereas the other is selected from:
Cl, F, OH, CF$_2$H, CF$_3$, OR$^{14}$ or SR$^{14}$, preferably OH, CF$_2$H, OR$^{14}$ or SCH$_3$, in particular OH or OC$_{1-3}$ alkyl, preferably OH or OCH$_3$, or, if R$^9$ and R$^{13}$ correspond to H and R$^{11}$ corresponds to OH, OCH$_3$, Cl or F, preferably Cl, one of R$^{10}$ or R$^{12}$ also corresponds to H, whereas the other corresponds to OH, OCH$_3$, Cl or F, preferably Cl, or if R$^9$, R$^{10}$, R$^{12}$ and R$^{13}$ correspond to H, R$^{11}$ is selected from CF$_3$, CF$_2$H, Cl or F, preferably F, or if R$^{10}$, R$^{11}$ and R$^{12}$ correspond to H, one of R$^9$ or R$^{13}$ also corresponds to H, whereas the other is selected from OH, OC$_2$H$_5$ or OC$_3$H$_7$, particularly preferably, if R$^9$, R$^{11}$ and R$^{13}$ correspond to H, one of R$^{10}$ or R$^{12}$ also corresponds to H, whereas the other is selected from:
Cl, F, OH, SH, CF$_2$H, CF$_3$, OR$^{14}$ or SR$^{14}$ preferably OH or OR$^{14}$, in particular OH or OC$_{1-3}$ alkyl, preferably OH or OCH$_3$.

In particular for compounds of group b), compounds of formula II are in the form of the diastereomers having the relative configuration IIa IIa in particular in mixtures having a relatively high content of this diastereomer in comparison to the other diastereomer, or are used as a pure diastereomer.

In particular for compounds of group b), compound A, which is selected from the following group, is used:
- (1RS,3RS,6RS)-6-dimethylaminomethyl-1-(3-methoxy-phenyl)-cyclohexane-1,3-diol,
- (+)-(1R,3R,6R)-6-dimethylaminomethyl-1-(3-methoxy-phenyl)-cyclohexane-1,3-diol,
- (1RS,3RS,6RS)-6-dimethylaminomethyl-1-(3-hydroxy-phenyl)-cyclohexane-1,3-diol,
- (1RS,3SR,6RS)-6-dimethylaminomethyl-1-(3-methoxy-phenyl)-cyclohexane-1,3-diol,
- (+)-(1R,2R,5S)-3-(2-dimethylaminomethyl-1-hydroxy-5-methyl-cyclohexyl)-phenol or (1RS,2RS,5RS)-3-(2-dimethylaminomethyl-1-hydroxy-5-trifluoromethyl-cyclohexyl)-phenol, preferably as the hydrochloride.

In a preferred embodiment, for the combination according to the invention, compound A in group c) is selected from compounds according to formula III, in which:

X is selected from

OH, F, Cl, OC(O)CH$_3$ or H, preferably OH, F or H, in particular F or H.

and/or $R^9$ to $R^{13}$, wherein three or four of the radicals $R^9$ to $R^{13}$ must correspond to H, independently of one another are selected from H, Cl, F, OH, CF$_2$H, CF$_3$ or saturated and unsubstituted, branched or unbranched C$_{1-4}$ alkyl; OR$^{14}$ or SR$^{14}$, where R$^{14}$ is selected from saturated and unsubstituted, branched or unbranched C$_{1-3}$ alkyl;

preferably H, Cl, F, OH, CF$_2$H, CF$_3$, OCH$_3$ or SCH$_3$ or $R^{12}$ and $R^{11}$ form a 3,4-OCH=CH ring, characterised in that, in particular, if $R^9$, $R^{11}$ und $R^{13}$ correspond to H, one of $R^{10}$ or $R^{12}$ also corresponds to H, whereas the other is selected from:

Cl, F, OH, CF$_2$H, CF$_3$, OR$^{14}$ or SR$^4$, preferably OH, CF$_2$H, OR$^{14}$ or SCH$_3$, in particular OH or OC$_{1-3}$ alkyl, preferably OH or OCH$_3$, or if $R^9$ and $R^{13}$ correspond to H and $R^{11}$ corresponds to OH, OCH$_3$, Cl or F, preferably Cl, one of $R^{10}$ or $R^{12}$ also corresponds to H, whereas the other corresponds to OH, OCH$_3$, Cl or F, preferably Cl, or if $R^9$, $R^{10}$, $R^{12}$ and $R^{13}$ correspond to H, $R^{11}$ is selected from CF$_3$, CF$_2$H, Cl or F, preferably F, or if $R^{10}$, $R^{11}$ and $R^{12}$ correspond to H, one of $R^9$ or $R^{13}$ also corresponds to H, whereas the other is selected from OH, OC$_2$H$_5$ or OC$_3$H$_7$, particularly preferably, if $R^9$, $R^{11}$ and $R^{13}$ correspond to H, one of $R^{10}$ or $R^{12}$ also corresponds to H, whereas the other is selected from:

Cl, F, OH, SH, CF$_2$H, CF$_3$, OR$^{14}$ or SR$^{14}$, preferably OH or OR$^4$, in particular OH or OC$_{1-3}$ alkyl, preferably OH or OCH$_3$.

In particular for compounds of group c), compounds of formula III are in the form of their diastereomers having the relative configuration IIIa IIIa in particular in mixtures having a relatively high content of this diastereomer in comparison to the other diastereomer, or are used as a pure diastereomer.

In particular for compounds of group c), compound A, which is selected from the following group, is used:

(+)-(1R,2R)-3-(2-dimethylaminomethyl-1-fluoro-cyclohexyl)-phenol, (+)-(1S,2S)-3-(2-dimethylaminomethyl-cyclohexyl)-phenol or (−)-(1R,2R)-3-(2-dimethylaminomethyl-cyclohexyl)-phenol, preferably as the hydrochloride.

In a preferred embodiment, for the combination according to the invention, the COX-II inhibitor (compound B) is selected from:

Celecoxib, Rofecoxib, Etoricoxib, Valdecoxib, Parecoxib, Etodolac, Meloxicam or Nimesulide, in particular Celecoxib or Rofecoxib.

The active ingredient combinations according to the invention are toxicologically safe, so the invention also relates to a pharmaceutical composition containing an active ingredient combination according to the invention; and optionally suitable additives and/or auxiliaries or active ingredients;

Suitable additives and/or auxiliaries, in the context of this invention, are any substances known to a person skilled in the art from the prior art for obtaining galenical formulations. The choice of these auxiliaries and the amounts thereof to be used depend on whether the pharmaceutical preparation is to be administered orally, intravenously, intraperitoneally, intradermally, intramuscularly, intranasally, buccally, rectally or topically. Preparations in the form of tablets, chewing tablets, dragees, capsules, granules, drops, juices or syrups are suitable for oral administration, solutions, suspensions, easily reconstitutable dry preparations and sprays are suitable for parenteral, topical and inhalative administration. Suppositories for rectal administration are a further possibility. Administration in a deposit, in dissolved form, in a carrier foil or a plaster, optionally with the addition of agents to promote skin penetration, are examples of suitable percutaneous administration preparations. Examples of auxiliaries and additives for oral administration preparations include blasting agents, lubricants, binders, fillers, mould release agents, optionally solvents, flavouring agents, sugar, in particular carrier agents, diluents, dyes, antioxidants, etc. Waxes and fatty acid esters may, inter alia, be used as suppositories and carrier substances, preservatives and suspension auxiliaries, etc. may be used as parenteral administration agents. The amount of active ingredient to be administered to the patient varies as a function of the weight of the patient, the method of administration and the severity of the illness. The compounds according to the invention may be released after a delay from preparations that may be administered orally, rectally or percutaneously. In the indication according to the invention, suitable retarding formulations, in the form of a "once-daily" preparation that only has to be taken once a day, are particularly preferred.

Also preferred are pharmaceutical compositions containing at least 0.05 to 90.0% of the active ingredient combination, in particular low effective doses, in order to prevent side effects or analgesic effects. Conventionally, 0.1 to 5000 mg of the combination per kg of body weight, in particular 1 to 500 mg per kg, preferably 2 to 250 mg per kg are administered. Also preferred and conventional, however, is the administration of 0.01 to 5 mg/kg, preferably 0.03 to 2 mg/kg, in particular 0.05 to 1 mg/kg of body weight.

Examples of auxiliaries may include: water, ethanol, 2-propanol, glycerol, ethylene glycol, propylene glycol, polyethylene glycol, polypropylene glycol, glucose, fructose, lactose, saccharose, dextrose, molasses, starch, modified starch, gelatine, sorbitol, inositol, mannitol, microcrystalline cellulose, methyl cellulose, carboxymethyl cellulose, cellulose acetate, shellac, cetyl alcohol, polyvinyl pyrrolidone, paraffins, waxes, natural and synthetic gums, acacia gum, alginates, dextran, saturated and unsaturated fatty acids, stearic acid, magnesium stearate, zinc stearate, glycerol stearate, sodium lauryl sulphate, edible oils, sesame oil, coconut oil, peanut oil, soybean oil, lecithin, sodium lactate, polyoxyethylene and polypropylene fatty acid ester, sorbitan fatty acid ester, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulphate, zinc sulphate, calcium sulphate, potash, calcium phosphate, dicalcium phosphate, potassium bromide, potassium iodide, talcum, kaolin, pectin, Crospovidon, agar und bentonite.

The pharmaceutical compositions according to the invention are produced using means, devices, methods and processes that are well known in the prior art of pharmaceutical formulations, as described for example in "Remington's Pharmaceutical Sciences", A. R. Gennaro (ed.), 17$^{th}$ edition, Mack Publishing Company, Easton, Pa. (1985), in particular in part 8, chapters 76 to 93.

Thus, for a solid formulation, such as a tablet, for example, the active ingredient of the pharmaceutical composition may be granulated with a pharmaceutical carrier, for example conventional tablet ingredients such as corn starch, lactose, saccharose, sorbitol, talcum, magnesium stearate, dicalcium phosphate or pharmaceutically acceptable gums, and pharmaceutical diluents, for example water, in order to form a solid composition that contains an active ingredient in homogeneous distribution. The term "homogeneous distribution" is taken to mean that the active ingredient is distributed uniformly over the entire composition, so that said composition may easily be divided into equally effective unit dose forms, such as tablets, pills or capsules. The solid composition is then divided into unit dose forms. The tablets or pills of the pharmaceutical composition according to the invention or of the compositions according to the invention may also be coated or compounded in a different manner, in order to provide a dose form with a delayed release. Suitable coating agents include polymer acids and mixtures of polymer acids with materials such as shellac, cetyl alcohol and/or cellulose acetate.

As it has proven particularly preferable if the COX-II inhibitor is given before giving the selected analgesic (compound A), in particular at least 30 minutes, preferably 1 hour beforehand, galenical formulations having a suitable release profile are particularly preferred. An example of this might be an osmotically driven release system for achieving a delayed release of compound A with a coating that contains the COX-II inhibitor and is released correspondingly earlier. In a release system of this kind, which is preferably oral, at least one, and preferably all, of the surfaces of the release system, preferably that or those that is/are or might be in contact with the release medium, is/are semipermeable, preferably equipped with a semipermeable coating, so the surface(s) is/are permeable to the release medium, but substantially, preferably entirely, impermeable to the active ingredient, compound A, the surface(s) and/or optionally the coating comprising at least one opening for releasing the active ingredient, compound A. Moreover, precisely that/those surface(s) that is/are in contact with the release medium is/are provided with a coating containing and releasing the COX-II inhibitor. This is preferably taken to mean a system in tablet form comprising a discharge opening, an osmotic pharmaceutical composition core, a semipermeable membrane and a polymer portion that exerts pressure. A good and preferred example of this kind of system is the OROS® System of the ALZA Corporation, USA, of which the website or other forms of product information contain details regarding the OROS® System. These are, in particular, the OROS® Push-Pull™ System, the OROS® Delayed Push-Pull™ System, the OROS® Multi-Layer Push-Pull™ system, the OROS® Push-Stick System and also, in specific cases, the L-OROS™. Embodiments and examples of the specific production of osmotically driven release systems may be inferred from U.S. Pat. Nos. 4,765,989, 4,783,337 and 4,612,008, all of the contents of which are part of the description of this invention.

A further example is a gel-matrix tablet, such as the products developed by Penwest Pharmaceuticals (for example, under TimeRX). Suitable examples are provided in U.S. Pat. Nos. 5,330,761, 5,399,362, 5,472,711 and 5,455,046. Particularly suitable is a retarding matrix formulation, with an inhomogeneous distribution of the active ingredient combination, the COX-II-inhibitor being found in propagated form in the outer region (the portion that comes into contact with the release medium most quickly) of the matrix and the selected analgesic (compound A) being found in propagated form inside the matrix. On contact with the release medium, the outer matrix layer initially (and relatively quickly) swells and firstly releases the COX-II inhibitor, followed by the significantly (more) retarded release of compound A. Examples of a suitable matrix include matrices with 1 to 80% by weight of one or more hydrophilic or hydrophobic polymers as pharmaceutically acceptable matrix formers. A further example of a suitable matrix may be inferred from DE 33 09 516 A1.

The invention also relates to the use of an active ingredient combination according to the invention for the treatment of pain, in particular neuropathic, acute, chronic, visceral or cancer pain.

The invention also relates to a method for the treatment of pain in which the active ingredient combination according to the invention is used.

A further preferred subject of the invention is a therapy, in particular a therapy regimen, in which, in order to treat pain, the COX-II inhibitor is given before giving the selected analgesic (compound A), as this has proven to be particularly advantageous. Particularly preferably, the COX-II inhibitor is given at least 30 minutes, preferably 1 hour before giving compound A. This may be done, for example, directly by the relevant doctor, but also (for example, on the doctor's instructions) by the patient himself. The active ingredient combination may also be separated into various pharmaceutical preparations, and may in particular also be in the form of various pharmaceutical packages. A possible and also advantageous embodiment of this invention would be a kit in which the active ingredients of the active ingredient combination according to the invention, although spatially separated, are provided in a presentation form, for example a pharmaceutical composition package. A "kit" of this type is accordingly also a preferred embodiment of the invention.

EXAMPLES

The following examples are intended to illustrate and clarify certain embodiments of the invention, however they are not intended to and should not be understood to limit the subject matter of the invention.

Example 1

Supra-Additive Effect in the Randall-Selitto Test

The compounds, which were tested with regard to their efficacy, are listed below. The numbering is used in the examples and the figures:

Compound A:

| Name | Compound No. |
|---|---|
| (1R,2R)-3-(2-dimethylaminomethyl-cyclohexyl)-phenol; hydrochloride | 1 |
| (1R,2R)-3-(3-dimethylamino-1-ethyl-2-methyl-propyl)-phenol; hydrochloride | 2 |
| (1S,2S)-3-(3-dimethylamino-1-ethyl-2-methyl-propyl)-phenol; hydrochloride | 3 |
| (1RS,3RS,6RS)-6-dimethylaminomethyl-1-(3-[methoxy-phenyl]-cyclohexane-1,3-diol; hydrochloride | 4 |

COX II-inhibitors:

| Name | Compound No. |
|---|---|
| Celecoxib | 101 |
| Rofecoxib | 102 |
| Celecoxib in the form of the final pharmaceutical composition CELEBREX ® | 103 |
| Rofecoxib in the form of the final pharmaceutical composition VIOXX ® | 104 |

Example 2

Writhing Test on Mouse

The writhing test is a modification of the method of Schmauss C and Yaksh TL, J Pharmacol Exp Ther 228: 1-12 (1984) and a model for acute pain.

9% acetic acid was administered to the animals intraperitoneally as a pain stimulus. This was administered 30 min (test substance perorally) or 10 min (test substance intravenously) after the administration of the test substance. The pain-induced writhing reactions were recorded 10 to 35 min after the administration of acetic acid. As rats rarely exhibit the conventional writhing reaction of mice, but do exhibit other very clear expressions of pain, the evaluation took place on the basis of a score division. Pain expressions, such as a slanting body angle when the animal stands upright, frequent cleaning of the belly or arching of the back without stretching of the rear limbs, were thus included in the evaluation.

The animals that had been treated with the substance were compared with a control group, which had been given physiological saline solution. The group contained 10 animals (n=10).

The result of the active ingredient combination of compound no. 2 with the COX-II inhibitors 101, 102, 103 and 104 may be inferred from Table 1.

Example 3

Formalin Test

The formalin test (Dubuisson, D. and Dennis, S. G., 1977, Pain, 4, 161 to 174) is a model for acute and chronic pain. In the tests presented here, the chronic pain component was evaluated.

By means of a single formalin injection into the dorsal side of a hind paw of test animals that were able to move freely, a biphasic nociceptive reaction, which was detected by the observation of three clearly distinguishable behavioural patterns, was induced.

Formalin having a volume of 20 μl and a concentration of 1% was administered subcutaneously into the dorsal side of the right hind paw of each animal. The specific behavioural changes, such as raising and shaking of the paw, weight loss in the animal and biting and licking reactions, were continuously observed and registered for up to 60 min after the formalin administration. The behavioural changes were weighted differently (a score of 0 to 3) and a pain rate (PR) calculated having the general formula:

$$PR=[(T_0 \times 0)+(T_1 \times 1)+(T_2 \times 2)+(T_3 \times 3)]/180.$$

$T_0$, $T_1$, $T_2$ and $T_3$ each correspond to the time in seconds during which the animal exhibited behavioural pattern 0, 1, 2 or 3. The group contained 10 animals (n=10).

The result of the active ingredient combination of compound no. 2 with the COX-II inhibitors 101, 102, 103 and 104 may be inferred from Table 1.

Example 4

Randell-Selitto Test

The Randell-Selitto test of Randall and Selitto (Arch. Int. Pharmacodyn., 1957, 111: 409 to 419) is a model for inflammatory pain.

By means of the injection of 0.1 ml 20% baking yeast suspension ventrally into a hind paw an oedema was induced, on which pain was generated 4 hours later by continuously increasing pressure with a stamp (2 mm tip diameter). The measured value to be determined and at the same time also the end point of the pain test was the pressure at which the vocalisation reaction of the animal occurred. The percentage maximum possible effect (%MPE) was calculated. The maximum pressure of the stamp was 250 g. The group size was n=10.

The results of the tests may be inferred from FIGS. 1 to 4 and the following Tables 1 to 4.

Evaluation:

The theoretical additive value was calculated by adding the mean values from the individual tests of the test substance and COX-II inhibitor. The corresponding standard deviation of the theoretical additive mean value was calculated from the addition of the variances.

In all of the above-listed animal models, the selected analgesics (compound A) exhibited a moderately strong to strong inhibition of nociception or hyperalgesia.

The simultaneous administration of a selective COX-II inhibitor (Rofecoxib or Celecoxib) with compound 1 resulted, in the listed tests, i.e. in acute, in chronic and in inflammatory pain (Table 1), in an intensification of effect in comparison to the theoretically calculated purely additive effect. A clear effect-increasing supra-additive effect is to be highlighted in the case of the staggered administration of COX-II inhibitor and the selected analgesics (compound A), compound nos. 1, 4, 2 and 2 (Randall-Selitto test). In these tests, either Rofecoxib or Celecoxib was administered 1 hour prior to the administration of the selected analgesic (compound A). In a few tests, Rofecoxib was administered as the final preparation Vioxx and Celecoxib as Celebrex.

The results of selected tests, in this case, for example, with compound no. 1, are summarised in the following table (Table 1): Fixed ratio combination: equieffective dose of the two substances, calculated from the ratio of the respective ED50 values. Fixed dose combination: fixed doses of the respective substances.

TABLE 1

| Test (animal model) | Compound No./ combination (compound A + COX II | Method of administration | Ratio of compound A (1) to COX-II inhibitor (2) 1: | 2: | Dose of compound A (1) and COX-II inhibitor (2) [mg/kg] 1: | 2: | % effect/ ED50 [mg/kg] of compound A | % effect/ ED50 [mg/kg] of COX-II inhibitor | % effect/ ED50 [mg/kg] of combination (theoretical additive value) | % effect/ ED50 [mg/kg] of combination (experimental value) |
|---|---|---|---|---|---|---|---|---|---|---|
| \multicolumn{11}{c}{Fixed ratio combination} |
| Writhing (rat) | 2 + 102 | peroral | 1 | 2 | — | — | $ED_{50}$: 33.0 | $ED_{50}$: 60.1 | $ED_{50}$: 47.0 | $ED_{50}$: 23.3 |
| Formalin test (mouse) | 2 + 101 | peroral | 47.3 | 52.7 | — | — | $ED_{50}$: 34.6 | $ED_{50}$: 38.5 | $ED_{50}$: 36.5 | $ED_{50}$: 22.8 |
| Formalin test (rat) | 2 + 101 | peroral | 10.5 | 89.5 | — | — | $ED_{50}$: 18.0 | $ED_{50}$: 154 | $ED_{50}$: 86.0 | $ED_{50}$: 60.6 |
| \multicolumn{11}{c}{Fixed dose combination:} |
| Randall-Selitto (rat) | 2 + 104 | peroral | — | — | 31 | 215 | 13.3 | 11.2 | 24.5 | 29.7 |
| Randall-Selitto (rat) | 2 + 101 | peroral | — | — | 31 | 215 | 13.3 | 9.8 | 23.1 | 29.6 |
| \multicolumn{11}{c}{Fixed dose combination (staggered administration; COX inhibitor 1 hour prior to compound A):} |
| Randall-Selitto (rat) | 2 + 104 | peroral | — | — | 31 | 215 | 20.0 | 13.0 | 33.0 | 45.7 |
| Randall-Selitto (rat) | 2 + 104 | peroral | — | — | 46 | 215 | 32.6 | 13.0 | 45.6 | 59.8 |
| Randall-Selitto (rat) | 2 + 103 | peroral | — | — | 31 | 215 | 20.0 | 17.3 | 37.3 | 60.9 |
| Randall-Selitto (rat) | 2 + 103 | peroral | — | — | 46 | 215 | 32.6 | 17.3 | 49.9 | 86.1 |

Table 2 shows the tests with compound No. 4 according to Example 4

TABLE 2

| Test (animal model) | Compound No./ combination (compound A + COX II) | Method of administration | Ratio of compound A (1) to COX-II inhibitor (2) 1: 2: | Dose of compound A (1) and COX-II inhibitor (2) 1: 2: | % effect/ ED$_{50}$ [mg/kg] of compound A | % effect/ ED$_{50}$ [mg/kg] of COX-II inhibitor | % effect/ ED$_{50}$ [mg/kg] of combination (theoretical additive value) | % effect/ ED$_{50}$ [mg/kg] of combination (experimental value) |
|---|---|---|---|---|---|---|---|---|
| Fixed dose combination (staggered administration; COX inhibitor 1 hour prior to compound A) ||||||||
| Randall-Selitto (rat) | 4 + 103 | peroral | — — | 68.1  215 | 85.4 15-75 min* | 16.7 15-75 min | 102.1 15-75 min | 109.3 15-75 min |
| Randall-Selitto (rat) | 4 + 103 | peroral | — — | 68.1  215 | 45.2 75-90 min* | 8.0 75-90 min | 53.2 75-90 min | 68.5 75-90 min |

Figure 1:
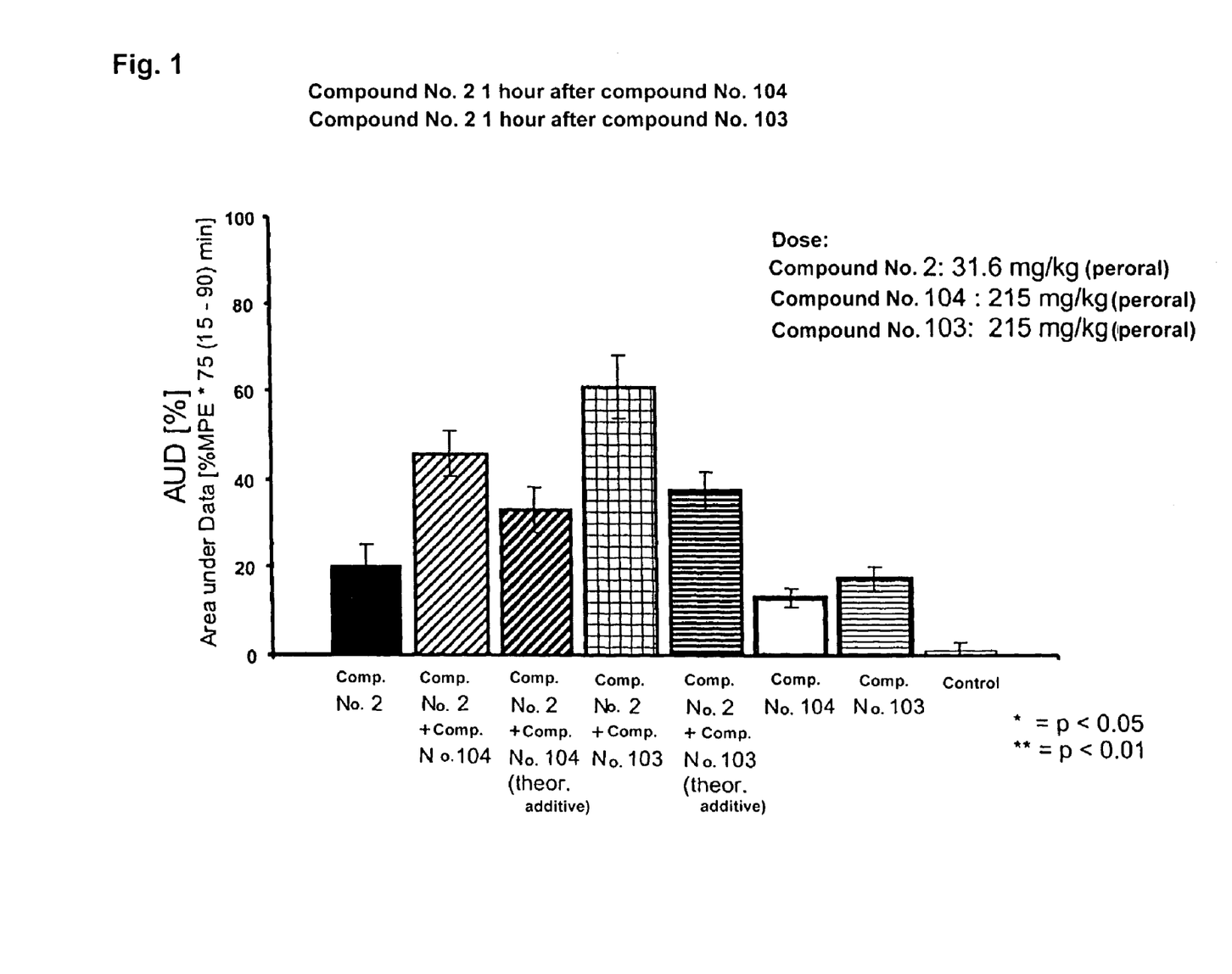
FIGS. 1 and 2: Supra-additive effect of the combination of the selected analgesic compound no. 2 (compound A) with the COX-II inhibitors in the Randall-Selitto test described below, in the case of staggered administration. The COX inhibitors (compound 104 or 103) were administered perorally to rats 1 hour before the administration of compound no. 2. AUD=area under data. %MPE=% of the maximum possible effect, wherein the maximum possible effect=100%.
Figure 2:
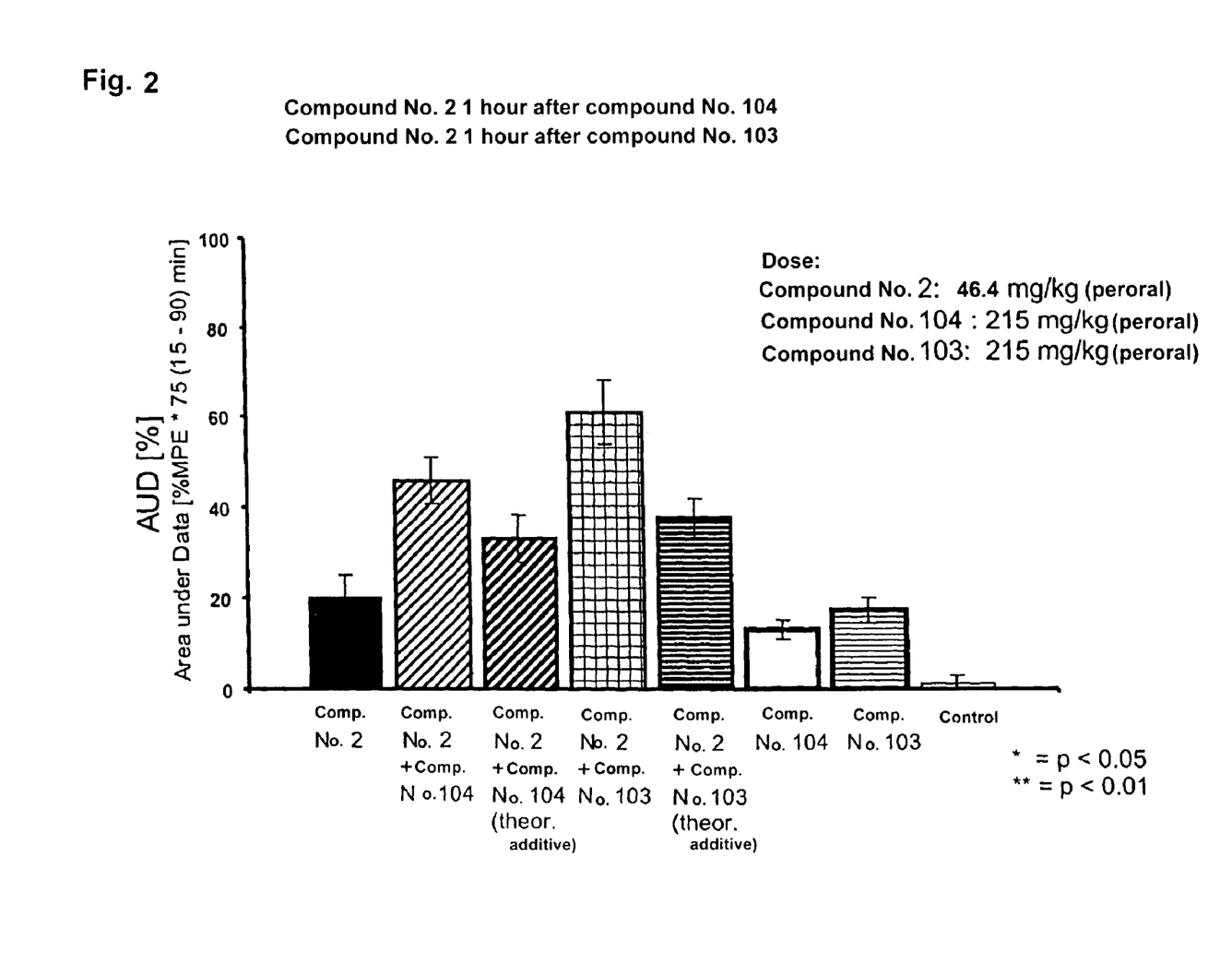
Figure 3:
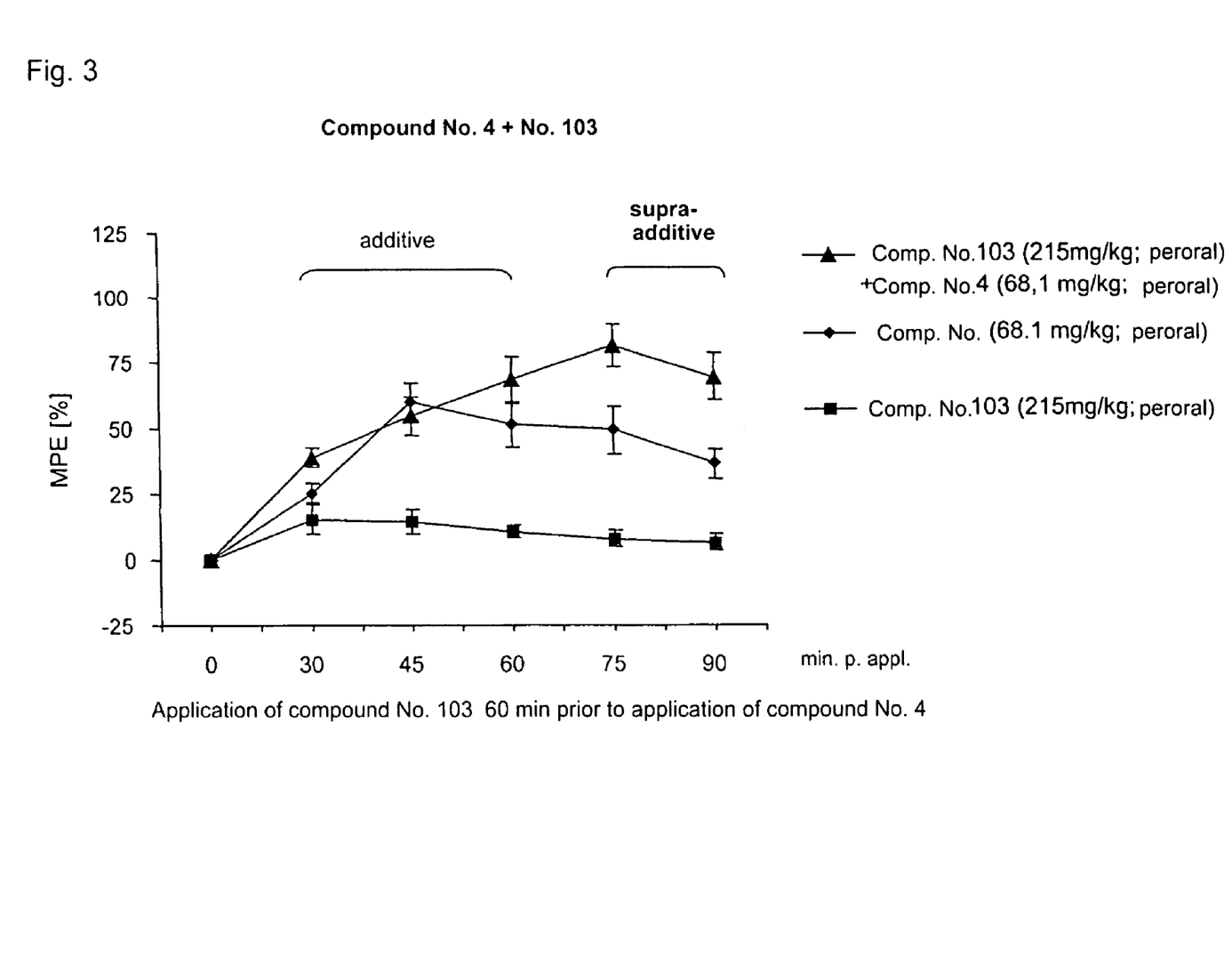
FIG. 3: Supra-additive effect of the combination of the selected analgesic compound no. 4 (compound A) with the COX-II inhibitor compound no. 103 in the Randall-Selitto test, in the case of staggered administration, over a period of 75 to 90 min after the administration of compound 4. The COX inhibitor was administered perorally to rats 1 hour before the administration of compound 4.
Figure 4:
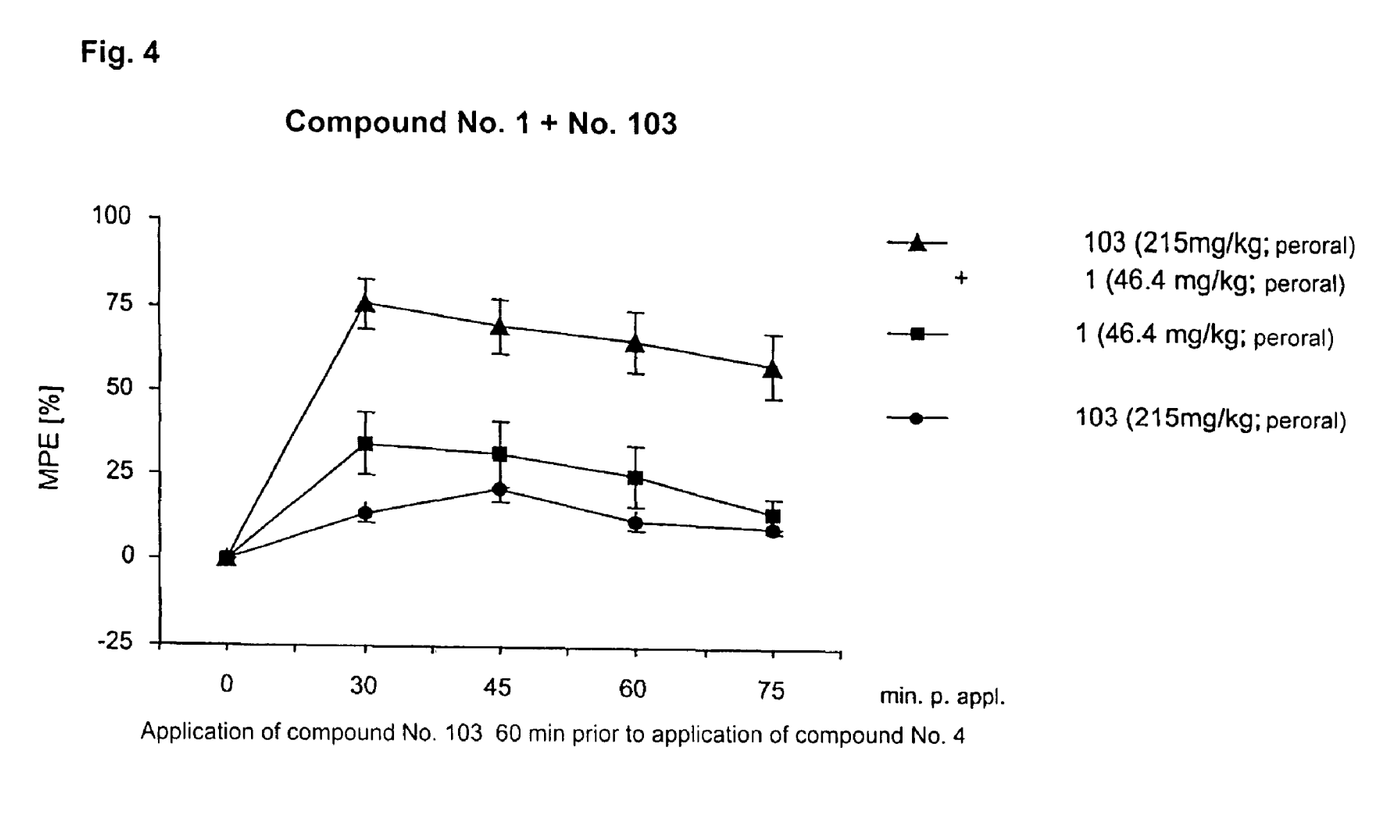
FIG. 4: Supra-additive effect of the combination of the selected analgesic compound no. 1 (compound A) with the COX-II inhibitor compound no. 103 in the Randall-Selitto test, in the case of staggered administration. The duration of the antinociceptive effect with the combination of compound no. 103 and compound no. 1 was also significantly extended. The COX inhibitor was administered perorally to rats 1 hour before the administration of compound no. 1.
Figure 5:
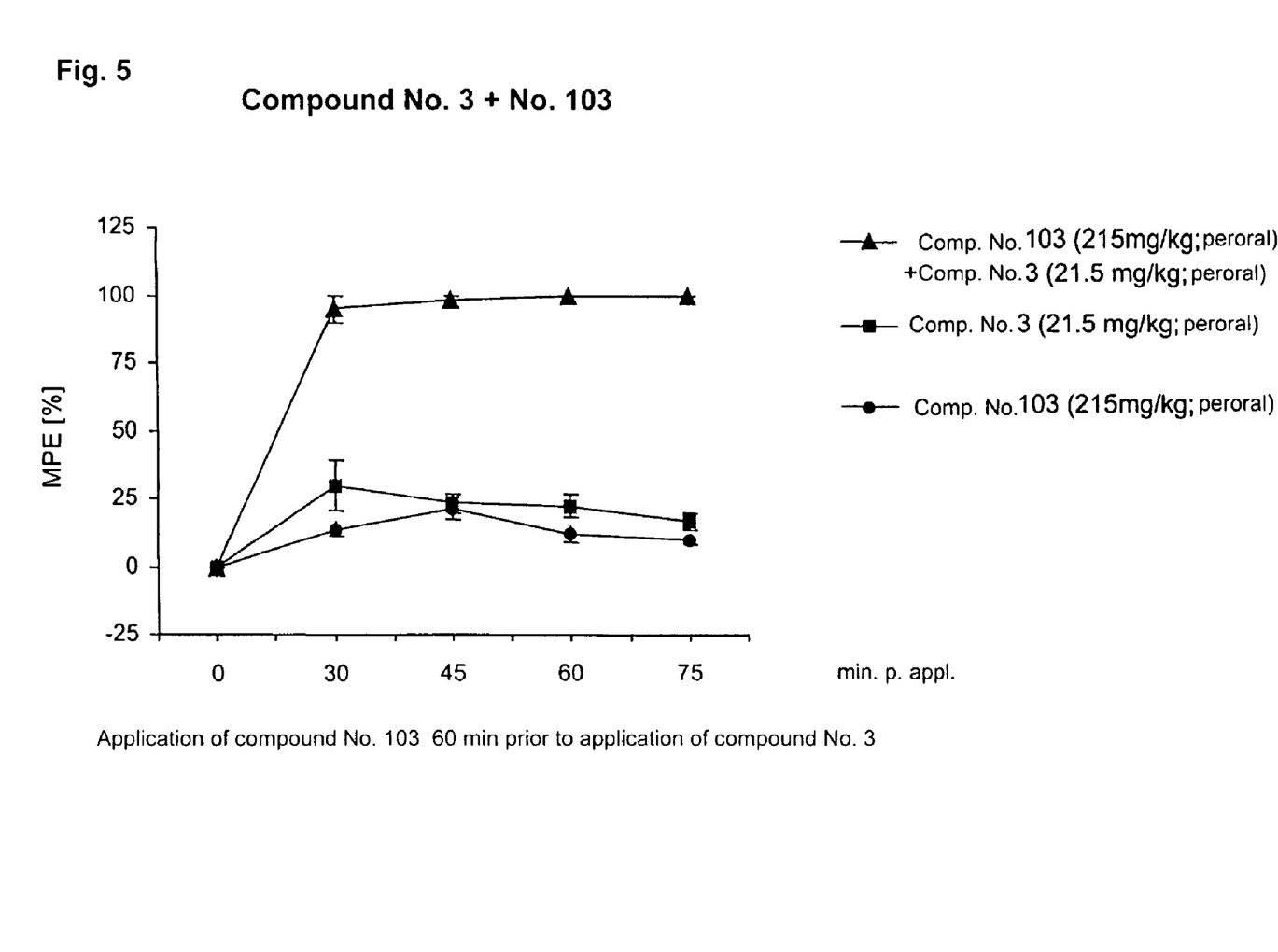
FIG. 5: Supra-additive effect of the combination of the selected analgesic compound no. 3 (compound A) with the COX-II inhibitor compound no. 103 in the Randall-Selitto test, in the case of staggered administration. The duration of the antinociceptive effect in the combination of compound no. 103 and compound no. 3 was also significantly extended. The COX inhibitor was administered perorally to rats 1 hour before the administration of compound no. 3.

* = evaluated period after administration of compound No. 4 (see FIG. 2)

Table 3 shows the tests with compound No. 1 according to Example 4

TABLE 3

| Test (animal model) | Compound No./ combination (compound A + COX II) | Method of administration | Ratio of compound A (1) to COX-II-inhibitor (2) 1: 2: | Dose of compound A (1) and COX-II inhibitor (2) 1: 2: | % effect/ ED$_{50}$ [mg/kg] of compound A | % effect/ ED$_{50}$ [mg/kg] of COX-II inhibitor | % effect/ ED$_{50}$ [mg/kg] of combination (theoretical additive value) | % effect/ ED$_{50}$ [mg/kg] of combination (experimental value) |
|---|---|---|---|---|---|---|---|---|
| Fixed dose combination (staggered administration; COX inhibitor 1 hour prior to compound A) ||||||||
| Randall-Selitto (rat) | 1 + 103 | peroral | — — | 46.4  215 | 26.2 | 8.9 | 35.1 | 84.1 |

Table 4 shows the tests with compound No. 3 according to Example 4

TABLE 4

| Test (animal model) | Compound No./ combination (compound A + COX II) | Method of administration | Ratio of compound A (1) to COX-II inhibitor (2) 1: 2: | Dose of compound A (1) and COX-II inhibitor 1: 2: | % effect/ ED$_{50}$ [mg/kg] of compound A | % effect/ ED$_{50}$ [mg/kg] of COX-II inhibitor | % effect/ ED$_{50}$ [mg/kg] of combination (theoretical additive value) | % effect/ ED$_{50}$ [mg/kg] of combination (experimental value) |
|---|---|---|---|---|---|---|---|---|
| Fixed dose combination (staggered administration; COX inhibitor 1 hour prior to compound A) ||||||||
| Randall-Selitto (rat) | 3 + 103 | peroral | — — | 21.5  21.5 | 22.8 | 8.9 | 31.7 | 96.4 |

Example 6

Parenteral Form of Administration 10 g (1R,2R)-3-(2-dimethylaminomethyl-cyclohexyl)-phenol; hydrochloride and 20 g Celecoxib were dissolved in 1 l water at room temperature for injection purposes and then adjusted to isotonic conditions by adding NaCl.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

The invention claimed is:
1. An active ingredient combination comprising synergistically effective amounts of at least one analgesic compound A and at least one COX-II inhibitor, where compound A is selected from the group consisting of:
   (1R,2R)-3-(3-dimethylamino-1-ethyl-2-methyl-propyl)-phenol; and
   (1S,2S)-3-(3-dimethylamino-1-ethyl-2-methyl-propyl)-phenol;
or a salt thereof with a physiologically tolerated acid, and where the COX-II inhibitor is selected from the group consisting of:
   celecoxib; and
   rofecoxib.

2. The active ingredient combination of claim 1, wherein compound A is present in the form of a hydrochloride.

3. The active ingredient combination of claim 1, wherein compound A is present in the form of a base.

4. The active ingredient combination of claim 1, wherein compound A is present in the form of a pure enantiomer or pure diastereoisomer.

5. The active ingredient combination of claim 1, wherein compound A is present in the form of a mixture of stereoisomers.

6. The active ingredient combination of claim 1, wherein compound A is present in the form of a racemic mixture.

7. A pharmaceutical formulation comprising an active ingredient combination according to claim 1 and a suitable auxiliary substance.

8. The pharmaceutical formulation of claim 7, further comprising at least one other active ingredient.

9. A method of alleviating pain in a mammal, said method comprising administering to said mammal an effective pain alleviating amount of an active ingredient combination according to claim 1.

10. The method of claim 9 wherein said pain is neuropathic, acute, chronic, visceral or cancer pain.

11. The method of claim 9, wherein said pain is inflammatory pain.

* * * * *